US005334615A

United States Patent [19]
Walles

[11] Patent Number: 5,334,615
[45] Date of Patent: Aug. 2, 1994

[54] OIL WITH BACTERICIDAL AND VIRUCIDAL PROPERTIES

[76] Inventor: Wilhelm E. Walles, 6648 N. River Rd., Freeland, Mich. 48623

[21] Appl. No.: 992,080

[22] Filed: Dec. 17, 1992

[51] Int. Cl.⁵ ............... A61K 31/335; A61K 31/08; A61K 31/11
[52] U.S. Cl. .............................. 514/467; 514/723; 514/705
[58] Field of Search ................. 514/467, 723, 705

[56] References Cited

U.S. PATENT DOCUMENTS

| | | | |
|---|---|---|---|
| 2,187,081 | 1/1940 | Hodgins et al. | 549/448 |
| 2,686,200 | 3/1952 | Cicero et al. | 549/448 |
| 3,072,524 | 1/1963 | Gäbelein | 514/463 |
| 3,223,713 | 12/1965 | Kesslin et al. | 549/448 |
| 3,412,160 | 11/1968 | Schierholt | 549/448 |
| 3,843,519 | 10/1974 | Manowitz | 514/467 |
| 4,448,977 | 5/1984 | Warner et al. | 568/483 |
| 4,835,178 | 5/1989 | Görler et al. | 514/463 |
| 4,861,764 | 8/1989 | Samour | 514/177 |
| 5,093,360 | 3/1992 | Yu | 514/463 |

FOREIGN PATENT DOCUMENTS

| | | |
|---|---|---|
| 3145709 | 5/1983 | Fed. Rep. of Germany . |
| 1129073 | 1/1957 | France . |
| 434078 | 11/1974 | U.S.S.R. . |
| 810182 | 5/1981 | U.S.S.R. . |
| 883043 | 11/1981 | U.S.S.R. . |
| 717418 | 10/1954 | United Kingdom . |
| 718502 | 11/1954 | United Kingdom . |
| 899065 | 6/1962 | United Kingdom . |
| 1291843 | 10/1972 | United Kingdom . |

OTHER PUBLICATIONS

Basmajian et al. (Eds.), "Stedman's Medical Dictionary, 24th Edition," Williams & Wilkins, Baltimore, 1982, pp. 334 & 810.
Chem Abst. 110(9):75525, Feb. 27, 1989.
Budavari et al. (Eds.), "The Merck Index, Eleventh Edition," Merck & Co., Rahway, N. J., 1989, pp. 685 & 702.

*Primary Examiner*—Frederick E. Waddell
*Assistant Examiner*—Gregory Hook
*Attorney, Agent, or Firm*—Christopher John Rudy

[57] ABSTRACT

A composition embraces an oil, for instance, a mineral oil, animal oil, or plant or vegetable oil, in combination with an acetal that can release aldehyde functionality on aqueous contact. It may be used in a method for kill or control of bacterium or virus for a suitable part of a human being or animal subject. For example, a 5% mineral oil and 2,2'-trimethylenebis(1,3-dioxolane) mixture can be used as a microbiocidal lubricant for drill bits in dentistry, or a suitably formulated composition may be used topically.

20 Claims, No Drawings

OIL WITH BACTERICIDAL AND VIRUCIDAL PROPERTIES

FIELD

The present invention concerns an aldehyde releasable lubricant useful in dentistry, surgery or medicine.

BACKGROUND

Dental tools such as probes, etc., are cleaned after use and immersed in a water solution of glutaraldehyde. The latter has been shown to kill bacteria and viruses.

High speed drills, as used in dentistry, need an oil lubricant such as mineral oil. They also hurl tiny bits of living cells into the air causing disease transfer problems only partially solved by wearing masks or gloves.

It would be desirable to combine oil and glutaraldehyde accordingly. However, this is not possible as water free glutaraldehyde polymerizes or decomposes rapidly.

Other problems in kill or control of bacteria or viruses in surgery, including for example oral surgery, and medicine yet exist where a lubricant or dressing would be applicable.

INVENTION SUMMARY

Provided hereby in one aspect is a composition of matter comprising an oil in combination with an acetal that can release aldehyde functionality on aqueous contact. Provided also in another aspect is a method for kill or control of bacterium or virus comprising providing a composition such as aforesaid for a suitable part of a human being or animal subject and thereby providing said kill or control.

The invention is useful in dentistry, surgery, medicine.

By it, significant advances are accomplished in the art. Now, nascent aldehyde functionality can be incorporated in oils without polymerization or decomposition from aldehyde, and, released upon contact with water or the like, it can be employed to locally destroy or ameliorate bacterial and/or viral populations or eliminate or reduce the propensity for bacterioliferous and/or viruliferous matter to undesirably convey its cargo. Dental and medical personnel may employ suitable composition embodiments as a lubricant, hand cream, or salve, etc., with the bactericidal or bacteriotoxic and/or virucidal or virutoxic effect. Dentists in particular may conduct drilling of teeth without excessive fear of bacterial or viral infection including from AIDS and hepatitis B viruses.

Numerous further advantages attend the invention.

ILLUSTRATIVE DETAILED EMBODIMENTS

The composition embraces an oil combined with an acetal. The acetal generally releases aldehyde functionality upon aqueous contact. Thus, the composition may do the same.

The composition is a mixture. Preferably, it is an essentially homogeneous mixture such as found in a colloidal dispersion or solution, especially the solution.

The oil may be any suitable hydrocarbon or substituted hydrocarbon containing sample, for example, as in a fatty acid ester, and is preferably hydrophobic at least to a substantial extent. The oil may be derived from animals or plants, for example, a tropical oil to include coconut or palm oil, a vegetable oil, or be a rock oil. It may be a liquid at room temperature. Desirably, it has a minimal if not essentially null amount of entrained water, other hydroxylated or carboxylic acid compounds, for example, as in a free fatty acid or a fatty alcohol, or other similar active hydrogen containing compounds or moieties such that may react with the combined acetal component prematurely. Advantageously, the oil is a mineral oil including either or both white (heavy) mineral oil or light (light white) mineral oil as known in dental and medicinal art. For an example, the mineral oil can be an aliphatic type.

The acetal is preferably an acetal of a terminal aldehyde and is desirably non-hydroxylated. Advantageously, it is a cyclic acetal of a terminal aldehyde, which provides for more stability and oil solubility especially in cases of 5 or 6-membered ring acetals. The acetal may be a diacetal compound such as of the following general formulae:

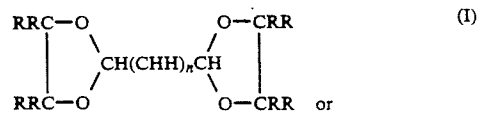

(I)

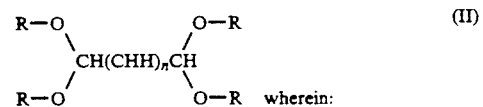

(II) wherein:

Each "n" is about from 2 to 8, most especially 3, and Each "R" includes independently at each occurrence lower alkyl to include methyl, ethyl or propyl including n-propyl, in formulae I & II, but especially hydro (H) in formula I.

Upon aqueous contact, i.e., contact of the acetal in the composition with water, cells, flesh, aldehyde functionality is released, which is to say, aldehyde is or may be formed or liberated at a perceptible rate. Accordingly, the solution preferred in the oil-phase composition is even more desired if the acetal is water soluble so that it can enter the aqueous phase in a state such as a solvated state to effect aldehyde formation or liberation and if the amount of acetal present in the oil-phase composition facilitates such or the like to the same or similar effect. For example, a mineral oil and 2,2'-trimethylenebis(1,3-dioxolane), i.e., TMBD, mixture upon aqueous contact may generally form or liberate aldehyde to presumably include glutaraldehyde along with a by product of ethylene glycol (two parts in the case of complete formation of one part of glutaraldehyde from one part TMBD in the aqueous contact).

Amounts of the oil and acetal may vary. Preferably, the amounts of acetal in the oil are about from 0.01 to 50 parts per hundred weight (pph or %), more preferably about from 0.1 to 20%, and most preferably about from 1 to 10%.

A preservative may be present or absent. As well, an acid catalyst may be present or absent, e.g., substantially.

The composition may be employed as a tool bit lubricant as for dentistry or surgery. It may be suitably formulated and employed as a topical dressing or ointment, skin cream, first aid cream, adhesive bandage component, surgical cream, or latex glove auxiliary component in dentistry or medicine.

SPECIFIC EMBODIMENTS

The following examples further illustrate the invention. Parts and percentages are by weight. Temperature is room.

EXAMPLE 1

Dental lubricating oil, sold commercially as Handpiece Lubricant 49730 (Buffalo Dental Mfg. Co.) and TMBD (Aldrich) are obtained. Combinations are made, as follows:

TABLE I

| | Oil-TMBD Combinations | | |
|---|---|---|---|
| Sample | Parts Oil | Parts TMBD | Solubility Characteristics |
| A1 | 97 | 3 | Totally clear, soluble. |
| B1 | 95 | 5 | Totally clear, soluble. |
| C1 | 93 | 7 | Generally clear with lower layer 2% TMBD* immiscible. |
| D1 | 90 | 10 | Generally clear with lower layer 5% TMBD* immiscible. |

*As is determined from a slightly different refractive index and slightly higher density, as are observed upon standing for 10 minutes. So, an at least approximately 5% oil-phase miscibility is established for room temperature. A 6 to 7% oil-phase miscibility value might be possible.

EXAMPLE 2

Water is mixed with TMBD, as follows:

TABLE II

| | Water-TMBD Combinations | | |
|---|---|---|---|
| Sample | Parts Water | Parts TMBD | Observation at 10 Minutes |
| A2 | 95 | 5 | Clear homogeneous mixture. |
| B2 | 90 | 10 | Clear homogeneous mixture. |
| C2 | 80 | 20 | Clear homogeneous mixture. |

Accordingly, an at least about 20% homogeneous mixture of water and TMBD and/or its reaction products is able to be produced. This means, in view of Example 1, at the interface of the oil-TMBD mixture and the bacteria, virus, saliva or tissue such as occurs during drilling, TMBD will nearly spontaneously transfer into the water phase and be converted into corresponding aldehyde, to presumably include glutaraldehyde, to kill or control the germs.

EXAMPLE 3

A 5% TMBD/95% Handpiece Lubricant 49730 solution, as from Example 1 Sample B1, is tested on plates (Petri dishes) for bactericidal and virucidal effect. A positive effect is observed for bacteria and for viruses generally more virile than HIV I (AIDS) and hepatitis B viruses. This shows that the present invention is effective for the kill or control of bacteria and viruses including the AIDS and hepatitis B type viruses.

EXAMPLE 4

A composition as of Example 1 Sample B1 and Example 3 is employed as a lubricant for a dental drill bit in drilling a tooth. Lubricating is favorable.

EXAMPLE 5

A composition of TMBD in oil is formulated and is used as a hand cream. The cream has a pleasant feel and can kill the AIDS virus.

CONCLUSION

The present invention is thus provided. Numerous adaptations and modifications can be effected within the spirit of the invention, the distinctly asserted scope of which is particularly pointed out as follows:

I claim:

1. A composition of matter comprising a substantially non-aqueous oil in combination with an acetal that can release aldehyde functionality on aqueous contact, wherein the acetal is saturated and non-hydroxylated, and wherein the acetal is selected from among compounds of the group consisting of compounds of the following general formulae:

$$\begin{array}{c} RRC-O \\ | \\ RRC-O \end{array} \diagdown CH(CHH)_nCH \diagup \begin{array}{c} O-CRR \\ | \\ O-CRR \end{array} \quad (I)$$

and $$\begin{array}{c} R-O \\ \\ R-O \end{array} \diagdown CH(CHH)_nCH \diagup \begin{array}{c} O-R \\ \\ O-R \end{array} \quad (II)$$

wherein:

Each "n" is 2 or 3, and

Each "R" is independently at each occurrence lower alkyl or hydro in the formula I and independently at each occurrence lower alkyl in the formula II.

2. The composition of claim 1, wherein each "n" is 3, and each "R" is hydro in the formula I and independently at each occurrence lower alkyl in the formula II.

3. The composition of claim 2, wherein the acetal is of the formula II wherein the "R" at each occurrence is ethyl.

4. The composition of claim 1, which is essentially a colloidal dispersion or solution.

5. The composition of claim 2, which is essentially a colloidal dispersion or solution.

6. The composition of claim 2, wherein the oil is a mineral oil.

7. The composition of claim 3, wherein the oil is a mineral oil.

8. The composition of claim 2, wherein the oil is an animal or plant oil, liquid at room temperature.

9. The composition of claim 3, wherein the oil is an animal or plant oil, liquid at room temperature.

10. The composition of claim 1, having no acid catalyst therein.

11. The composition of claim 2, wherein the acetal is of the formula I.

12. The composition of claim 1, which is useful for kill or control of bacterium or virus when provided in an amount effective to kill or control bacterium or virus, for a suitable part of a human being or animal subject, epidermally and/or integumentally, but extraneous said human being or animal subject, under conditions such that, when said composition contacts water proximate to said bacterium or virus or contacts said bacterium or virus itself, said kill or control is thus and there provided.

13. A composition of matter comprising mineral oil and 2,2'-trimethylenebis(1,3-dioxolane), in homogeneous mixture.

14. The composition of claim 13, which is a solution.

15. The composition of claim 13, which consists essentially of said oil and dioxolane.

16. The composition of claim 14, which consists essentially of said oil and dioxolane.

17. A method for kill or control of bacterium or virus comprising providing a composition of matter embracing a substantially non-aqueous oil in combination with an acetal that can release aldehyde functionality on aqueous contact, said acetal being selected from among compounds of the group consisting of compounds of the following general formulae:

$$\begin{array}{c} RRC-O \\ | \\ RRC-O \end{array} \diagdown CH(CHH)_n CH \diagup \begin{array}{c} O-CRR \\ | \\ O-CRR \end{array} \quad (I)$$

and $$\begin{array}{c} R-O \\ \diagdown \\ R-O \end{array} \diagup CH(CHH)_n CH \diagdown \begin{array}{c} O-R \\ \diagup \\ O-R \end{array} \quad (II)$$

wherein:

each "n" is 3, and
each "R" is hydro in the formula I and independently at each occurrence lower alkyl in the formula II;
and said acetal in said oil of said composition being provided in an amount effective to kill or control bacterium or virus, for a suitable part of a human being or animal subject, epidermally and/or integumentally, but extraneous said human being or animal subject, under conditions such that, when said composition contacts water proximate to said bacterium or virus or contacts said bacterium or virus itself, said kill or control is thus and there provided.

18. The method of claim 17, employing the composition in dentistry or oral surgery drilling as a drill bit lubricating oil.

19. The method of claim 18, done on teeth in dentistry.

20. The method of claim 17, which employs the composition in medicine as a topical ointment.

* * * * *